United States Patent [19]

Zaiger

[11] Plant 4,109

[45] Sept. 20, 1977

[54] PEACH TREE

[76] Inventor: Chris Floyd Zaiger, 537 Rosemore Ave., Modesto, Calif. 95351

[21] Appl. No.: 719,667

[22] Filed: Sept. 1, 1976

[51] Int. Cl.[2] ..... A01H 5/03

[52] U.S. Cl. ..... Plt./43

[58] Field of Search ..... Plt./43

*Primary Examiner*—Robert E. Bagwill

[57] ABSTRACT

A variety of peach tree which is of large size, vigorous growth; the tree being a productive and regular bearer of large, firm, yellow flesh, early ripening clingstone fruit, with a high degree of red skin color.

1 Drawing Figure

ORIGIN OF VARIETY

The new variety of peach tree was originated by me in my experimental orchard at Modesto, Calif. It was selected from a number of second generation seedlings of a cross between Ruby Gold nectarine (U.S. Plant Pat. No. 3,101) and a peach seedling of unknown parentage.

ASEXUAL REPRODUCTION OF THE VARIETY

The present variety was asexually propagated by grafting and budding, as performed at Modesto, Calif., shows that said characteristics described above proved to be identical with the original peach tree. I maintained the selection under careful and continual observation, during which time I recognized its distinct and desirable characteristics described above and selected the variety for reproduction.

SUMMARY OF THE VARIETY

My invention relates to a new and distinct variety of peach which bears yellow flesh clingstone fruit, characterized by early ripening, a high degree of red skin color and greater firmness than the present commercial varieties within this ripening period. The ripening period being approximately 3 to 4 days later than Armgold peach, (U.S. Plant Pat. No. 2,399). The new variety is further characterized by having fruit that colors two to three weeks before ripening, having large, firm, more highly colored fruit than other early varieties.

PHOTOGRAPHS OF VARIETY

The accompanying photographs show typical specimens of the foliage and fruit of my new variety, with upper and lower surfaces of the foliage being illustrated and exterior and a sectional view of the fruit being shown. These illustrations were taken shortly after being picked at maturity (shipping ripe) and the color are as nearly true as reasonably possible in color representations of this type.

DESCRIPTION OF THE VARIETY

The following is a detailed description of the foliage and fruit of my new variety, as based upon observations of specimens grown at Modesto, Calif., with color terminology in accordance with Reinhold Color Atlas by A. Kornerup and J. H. Wanscher.

Tree:
- *Size.*—Large.
- *Vigor.*—Vigorous.
- *Form.*—Spreading.
- *Production.*—Productive.

- *Bearing.*—Regular.

Trunk:
- *Size.*—Medium to stocky.
- *Surface.*—Medium to shaggy.

Branches:
- *Size.*—Medium to stocky.
- *Surface.*—Medium shaggy.
- *Color.*—Brown to grayish brown.
- *Lenticels.*—Medium quantity.

Leaves:
- *Size.*—Average length 7 inches. Average width 1⅜ inches.
- *Texture.*—Smooth.
- *Margin.*—Crenate.
- *Petiole.*—Medium length.
- *Glands.*—Reniform.
- *Color.*—Upper surface — Jade Green (27-E-4) to (27-E-5). Lower surface — Grayish green (29-D-5).

Flower buds:
- *Size.*—Large.
- *Length.*—Medium.

Flowers:
- *Size.*—Large, showy.
- *Color.*—Pink.
- *Pollen.*—Present.
- *Blooming period.*—Mar. 1, 1976 to Mar. 14, 1976.

Fruit:
- *Maturity when described.*—Hard ripe.
- *Date of first picking.*—May 27, 1976.
- *Date of last picking.*—June 6, 1976.
- *Size.*—Large; Diameter axially 2 5/16" to 3"; Suture plane 2⅜" to 3".
- *Form.*—Uniform. Symmetrical. Globose.
- *Suture.*—Shallow — extends from base to apex, with slight depression beyond pistil point.
- *Ventral surface.*—Rounded and only very slightly lipped.
- *Cavity.*—Rounded; Average depth — ⅜"; Average breadth — 1".
- *Apex.*—Short.

Skin:
- *Thickness.*—Medium thickness.
- *Texture.*—Tough. Tenacious to flesh.
- *Tendency to crack.*—None.
- *Down.*—Moderate.
- *Color.*—Bright yellow ground color (4-A-8) to (5-A-7) overspread with red (8-B-8 to lake red 9-C-8).

Flesh:
- *Amygdalin.*—Undetected.
- *Juice.*—Moderate.
- *Texture.*—Firm; meaty.

*Ripens.*—Uniform.
*Flavor.*—Mild.
*Aroma.*—Distinct.
*Eating quality.*—Excellent.
*Color.*—Melon yellow (5-A-6) to cadmium orange (5-A-8).

Stone:

*Type.*—Cling; Adheres to flesh over nearly entire surface.
*Size.*—Medium to large; Average length 1½"; Average width 1⅛"; Average thickness ¾".
*Form.*—Ovoid.
*Base.*—Straight.
*Apex.*—Acute.
*Sides.*—Equal.
*Surface.*—Pitted.
*Ridges.*—Rounded.
*Tendency to split.*—Slight.

*Color.*—Light tan.
Use: Market; Dessert.
Keeping quality: Excellent.
Shipping quality: Excellent.

The tree and its fruit herein described may vary in slight detail due to climatic and soil conditions under which this variety may be grown; the present description being of the variety as grown in the Central Valley of California.

The following is claimed:

1. A new and distinct variety of peach tree, as illustrated and described, which bears large, yellow flesh, clingstone fruit of early maturity. The fruit is further characterized in comparison with other early maturing varieties, by having greater firmness and a higher degree of red color, with excellent shipping quality.

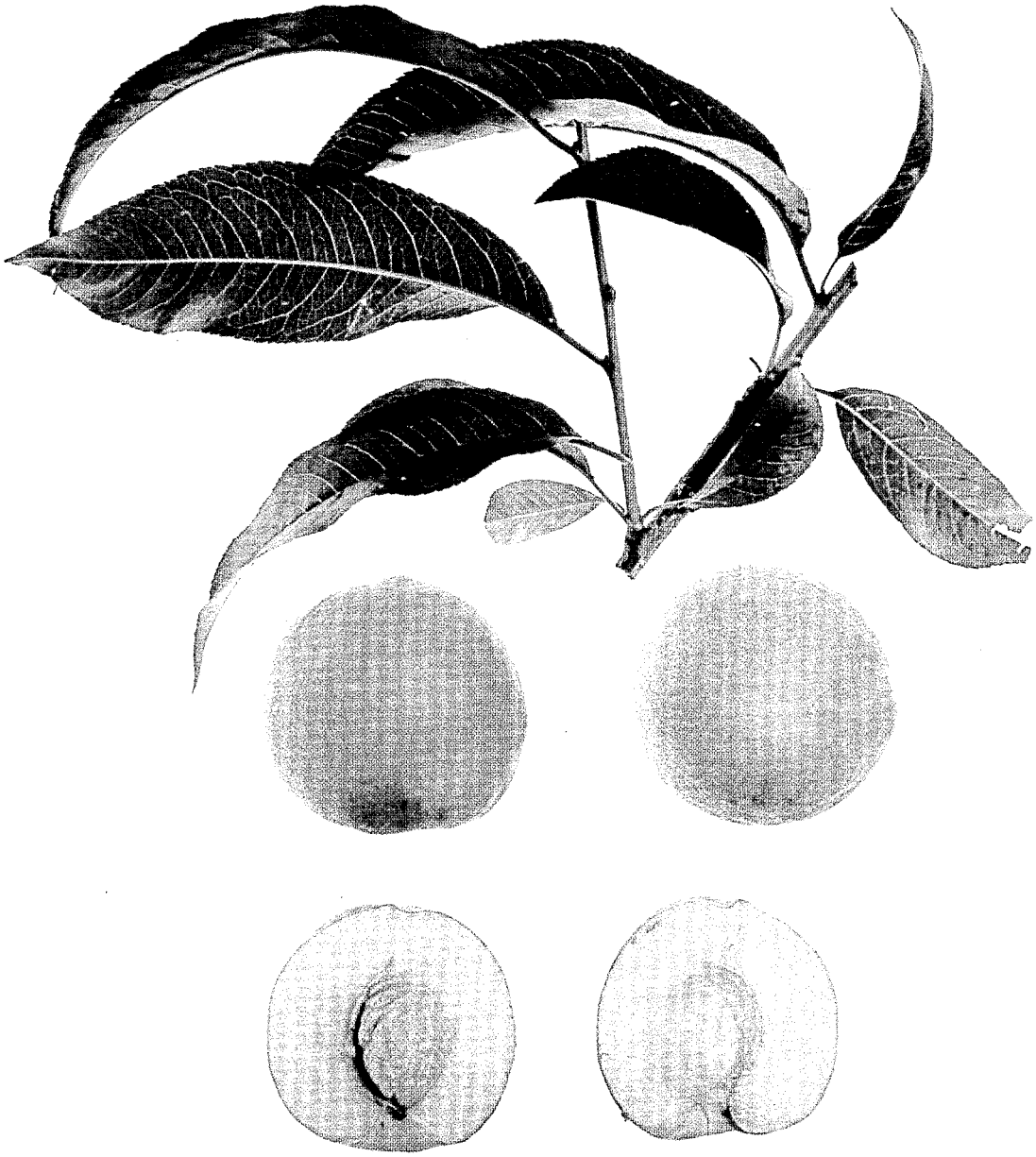

* * * * *